(12) United States Patent
Takei et al.

(10) Patent No.: US 8,329,845 B2
(45) Date of Patent: Dec. 11, 2012

(54) DIVIDED REDOX-CURING TYPE COMPOSITION

(75) Inventors: Mitsuru Takei, Kurashiki (JP); Hidemi Nakayama, Kurashiki (JP); Hiroki Shinoda, Chiyoda-ku (JP)

(73) Assignee: Kuraray Noritake Dental Inc., Kurashiki-shi (JP)

( * ) Notice: Subject to any disclaimer, the term of this patent is extended or adjusted under 35 U.S.C. 154(b) by 486 days.

(21) Appl. No.: 12/524,043

(22) PCT Filed: Jan. 16, 2008

(86) PCT No.: PCT/JP2008/050399
§ 371 (c)(1),
(2), (4) Date: Nov. 6, 2009

(87) PCT Pub. No.: WO2008/090784
PCT Pub. Date: Jul. 31, 2008

(65) Prior Publication Data
US 2010/0087613 A1    Apr. 8, 2010

(30) Foreign Application Priority Data
Jan. 23, 2007 (JP) .................. 2007-012740

(51) Int. Cl.
*C08F 222/14* (2006.01)
*C08F 220/26* (2006.01)
*C08F 12/24* (2006.01)
*A61K 6/08* (2006.01)

(52) U.S. Cl. .................. 526/318.43; 526/320; 526/313; 523/116

(58) Field of Classification Search ............. 526/318.43, 526/320, 313; 523/116, 117
See application file for complete search history.

(56) References Cited

U.S. PATENT DOCUMENTS

| | | | |
|---|---|---|---|
| 4,368,043 A | 1/1983 | Yamauchi et al. | |
| 4,540,722 A | 9/1985 | Bunker | |
| 6,583,197 B1 | 6/2003 | Wada et al. | |
| 6,818,682 B2 * | 11/2004 | Falsafi et al. | 523/116 |
| 2003/0018098 A1 * | 1/2003 | Falsafi et al. | 523/116 |
| 2008/0081889 A1 | 4/2008 | Kawashima et al. | |

FOREIGN PATENT DOCUMENTS

| | | |
|---|---|---|
| EP | 0 061 240 A2 | 9/1982 |
| EP | 1 066 813 A2 | 1/2001 |
| EP | 1 780 223 A1 | 5/2007 |
| JP | 53-67740 | 6/1978 |
| JP | 57-168903 | 10/1982 |
| JP | 58-125710 | 7/1983 |
| JP | 62-027403 | 2/1987 |
| JP | 62 27403 | 2/1987 |
| JP | 62027403 A * | 2/1987 |
| JP | 62 161709 | 7/1987 |
| JP | 62-161709 | 7/1987 |
| JP | 63-250310 | 10/1988 |
| JP | 63 250310 | 10/1988 |
| JP | 1 93507 | 4/1989 |
| JP | 01-093507 | 4/1989 |
| JP | 1 230508 | 9/1989 |
| JP | 01-230508 | 9/1989 |
| JP | 2001 72523 | 3/2001 |
| WO | WO 2006/016545 A1 | 2/2006 |

* cited by examiner

*Primary Examiner* — Michael M Bernshteyn
(74) *Attorney, Agent, or Firm* — Oblon, Spivak, McClelland, Maier & Neustadt, L.L.P.

(57) ABSTRACT

The present invention provides a divided redox-curing type composition including a first part in which at least an oxidizing agent (b) is dissolved in a first radical monomer including a radical monomer (a) having an acidic group and/or a hydrophilic group; and a second part in which at least an aromatic sulfinate (d) is dispersed in a second radical monomer including a radical monomer (c) having neither an acidic group nor a hydrophilic group. According to the present invention, a redox-curing type composition capable of securing a time necessary for an adhesion operation and exhibiting high bond strength not only at the initial stage of adhesion but also over a long period of time thereafter in application to a wetting material such as a tooth or a bone as well as a tooth crown repairing material such as a metal or porcelain.

17 Claims, No Drawings

DIVIDED REDOX-CURING TYPE COMPOSITION

TECHNICAL FIELD

The present invention relates to a divided redox-curing type composition.

BACKGROUND ART

An adhesive material has been used for repairing/curing a wetting material containing moisture (hereinafter simply referred to as a "wetting material") such as a biological hard tissue of a tooth, a bone or the like. As the adhesive material used for a wetting material, a resin-based curable composition including a radical monomer, a polymerization initiator and the like is widely used.

With respect to the resin-based curable composition, roughly divided two kinds of proposals have been conventionally made for improving the adhesiveness to a wetting material and to a biological hard tissue in particular. Specifically, one of the proposals is made with regard to a radical monomer including an acidic group with the intention of improving the chemical/physical interaction with a matrix of a tooth, a bone or the like to be adhered (see, for example, Patent Document 1), and the other proposal is made with regard to a polymerization initiator with the intention of efficiently polymerically curing, on a biological hard tissue, a curable composition including a radical monomer having an acidic group (see, for example, Patent Document 2).

When a resin-based curable composition is adhered onto a wetting material, sufficient bond strength cannot be attained in many cases because of curing inhibition caused by oxygen present on the adhesion interface. Such curing inhibition is caused seriously particularly when a curable composition is adhered onto dentin of a tooth or a bone including a large amount of oxygen.

Therefore, in order to accelerate the polymerization curing reaction while suppressing the curing inhibition derived from oxygen included in a wetting material, use of a redox polymerization initiator including a catalyst (an oxidizing agent) and an accelerator (a reducing agent) has been proposed. As the accelerator, a reducing compound including sulfur is regarded particularly promising (see, for example, Patent Documents 3 and 4).

Patent Document 3 proposes a redox-curing type aqueous polymeric composition composed of a first part including water-containing ethanol, sulfite, tertiary amine and the like and a second part including a free radical liquid monomer and a catalyst. Also, Patent Document 4 proposes a redox-curing type aqueous dental adhesive composition composed of a first part including a polymeric phosphorus compound, a polymerization catalyst and a diluent, a second part including aqueous ethanol, a sulfur compound and tertiary amine and a third part including aqueous ethanol and a soluble metal salt such as $FeCl_3$. Such a divided redox-curing type aqueous curable composition is used with the divided parts mixed into one mixture before use.

The redox-curing type aqueous curable compositions described in Patent Documents 3 and 4 have, however, an antinomic problem. Specifically, when the amount of the accelerator such as sulfite or tertiary amine is increased for increasing the bond strength to a wetting material, the redox reaction (the oxidation-reduction reaction) is so rapidly proceeded that the working time is extremely too short for practical use. On the contrary, when the amount of the accelerator is reduced for securing a time necessary for an adhesion operation, sufficient curing cannot be attained and the bond strength to a wetting material is low.

It is a redox-curing type nonaqueous curable composition described in Patent Document 5 that overcomes the aforementioned antinomic problem of the redox-curing type aqueous curable compositions described in Patent Documents 3 and 4. The redox-curing type nonaqueous curable composition includes a liquid radical monomer, an organic peroxide and a powdered water-soluble reducing compound with the powdered water-soluble reducing compound dispersed in the liquid radical monomer. Specific examples of the powdered water-soluble reducing compound are described as powders of sulfite, hydrogensulfite, pyrosulfite, thiosulfite, thionate and dithionite (see Patent Document 5, paragraph [0038]). According to the description of Patent Document 5, polymerization inhibition caused by oxygen included in a wetting material is a phenomenon occurring not within a curable composition but on an adhesion interface between the curable composition and the wetting material, and therefore, when the aforementioned composition is employed, the redox reaction can be selectively accelerated merely on the adhesion interface where the polymerization inhibition is caused, resulting in improving the bond strength to the wetting material without largely reducing the working time.

Patent Document 1: Japanese Laid-Open Patent Publication No. 53-67740

Patent Document 2: Japanese Laid-Open Patent Publication No. 45-29195

Patent Document 3: Japanese Laid-Open Patent Publication No. 57-168903

Patent Document 4: Japanese Laid-Open Patent Publication No. 58-125710

Patent Document 5: WO2006/016545

DISCLOSURE OF THE INVENTION

Problems to be Solved by the Invention

The redox-curing type nonaqueous curable composition described in Patent Document 5 has overcome the antinomic problem of the conventional redox-curing type aqueous curable composition by dispersing the powdered water-soluble reducing compound in the liquid radical monomer. It has been found, however, through examinations made by the present inventors that this redox-curing type nonaqueous curable composition should be further improved in its bond durability in application to a tooth crown repairing material such as a metal, porcelain, ceramics or a composite resin cured substance although it exhibits high bond durability in application to a wetting material such as a tooth or a bone.

Accordingly, the present inventors have earnestly studied for overcoming this problem, resulting in finding that a redox-curing type composition exhibiting high adhesiveness and high bond durability not only in the application to a wetting material such as a tooth or a bone but also in the application to a tooth crown repairing material such as a metal or porcelain can be obtained by using a specific reducing agent as a reducing agent of a redox catalyst and employing a specific composition.

The present invention was devised on the basis of the aforementioned finding, and an object of the invention is providing a divided redox-curing type composition capable of securing a time necessary for an adhesion operation and exhibiting high bond strength not only at the initial stage of adhesion but also over a long period of time thereafter in application to a wetting material as well as a tooth crown repairing material.

Means for Solving the Problems

The divided redox-curing type composition of claim 1 includes a first part in which at least an oxidizing agent (b) is dissolved in a first radical monomer including a radical monomer (a) having an acidic group and/or a hydrophilic group; and a second part in which at least an aromatic sulfinate (d) is dispersed in a second radical monomer including a radical monomer (c) having neither an acidic group nor a hydrophilic group. It is noted that the expression "having an acidic group and/or a hydrophilic group" is herein used as comprehensive expression including three cases of "having an acidic group but no hydrophilic group", "having a hydrophilic group but no acidic group" and "having both an acidic group and a hydrophilic group".

The divided redox-curing type composition of claim 2 is the divided redox-curing type composition of claim 1 in which a content of the radical monomer (a) having an acidic group and/or a hydrophilic group in the first radical monomer is 1 through 100 wt %, a content of the radical monomer (c) having neither an acidic group nor a hydrophilic group in the second radical monomer is 60 through 100 wt %, a content of the oxidizing agent (b) in the first part is 0.01 through 10 parts by weight based on 100 parts by weight of the first radical monomer, a content of the aromatic sulfinate (d) in the second part is 0.1 through 20 parts by weight based on 100 parts by weight of the second radical monomer, and a weight ratio for mixing the first part and the second part is 1:10 through 5:1.

The divided redox-curing type composition of claim 3 is the divided redox-curing type composition of claim 1 in which the radical monomer (a) having an acidic group and/or a hydrophilic group has at least one acidic group selected from the group consisting of a phosphoric group, a pyrophosphoric group, a thiophosphoric group, a phosphonic group, a sulfonic group and a carboxylic group, and/or a hydrophilic group.

The divided redox-curing type composition of claim 4 is the divided redox-curing type composition of claim 1 in which the radical monomer (a) having an acidic group and/or a hydrophilic group is at least one radical monomer selected from the group consisting of 10-(meth)acryloyloxydecyl dihydrogen phosphate, 1,3-di(meth)acryloyloxypropyl dihydrogen phosphate, 2-(meth)acryloyloxyethyl dihydrogen phosphate, 4-(meth)acryloyloxyethyl trimellitate anhydride, 4-(meth)acryloyloxyethyl trimellitate, 2-(meth)acrylamide-2-methylpropane sulfonate, 11-(meth)acryloyloxyundecane-1,1-dicarboxylic acid, bisphenol A diglycidyl (meth)acrylate, 2-hydroxyethyl(meth)acrylate, glycerol di(meth)acrylate and 1,2-bis[3-(meth)acryloyloxy-2-hydroxypropyloxy]ethane.

The divided redox-curing type composition of claim 5 is the divided redox-curing type composition of claim 1 in which the radical monomer (c) having neither an acidic group nor a hydrophilic group is a radical monomer having two or more radical polymeric groups.

The divided redox-curing type composition of claim 6 is the divided type redox-curing type composition of claim 5 in which the radical monomer having two or more radical polymeric groups is at least one radical polymeric monomer selected from the group consisting of 2,2-bis[4-(meth)acryloyloxypolyethoxyphenyl]propane, neopentyl glycol di(meth)acrylate, triethylene glycol di(meth)acrylate, [2,2,4-trimethylhexamethylene]bis(2-carbamoyloxyethyl)di(meth)acrylate, N,N'-(2,2,4-trimethylhexamethylene) bis[2-(aminocarboxy)propane-1,3-diol]tetra(meth)acrylate and 1,10-decanediol di(meth)acrylate.

Hereinafter, the divided redox-curing type compositions according to any of claims 1 through 6 may be generically designated as the present composition.

The dental adhesive of claim 7 includes the divided redox-curing type composition of claim 1.

Effects of the Invention

The present invention provides a redox-curing type composition capable of securing a time necessary for an adhesion operation and exhibiting high bond strength not only at the initial stage of adhesion but also over a long period of time thereafter in application to a wetting material such as a tooth or a bone as well as a tooth crown repairing material such as a metal or porcelain. The reason is as follows:

Since the polymerization inhibition is caused by oxygen on the adhesion interface between a redox-curing type composition and a wetting material, the polymerization curability is lower on the adhesion interface than within the composition. In a conventional aqueous curable composition, when a large amount of water-soluble reducing compound is dissolved in the aqueous curable composition for improving the polymerization curability attained on the adhesion interface, the polymerization curability within the composition, which need not be improved, is simultaneously improved, and therefore, the curing time of the entire composition is shortened, resulting in a difficulty in securing a time necessary for an adhesion operation. Alternatively, in the conventional aqueous curable composition, when the amount of water-soluble reducing composition to be dissolved in the aqueous curable composition is reduced for securing a time necessary for an adhesion operation, it is difficult to attain sufficient adhesiveness to a wetting material and particularly to a biological hard tissue such as dentin including a large amount of oxygen. On the contrary, in the present composition, an aromatic sulfinate (d) existing on the adhesion interface is dissolved in water present on the surface of a wetting material due to its water-solubility. Since the aromatic sulfinate (d) dissolved in the water and an oxidizing agent (b) dissolved in a first radical monomer are both in a dissolved state, they meet with each other highly frequently in a molecule state. In other words, a radical generation reaction (a redox reaction) caused on the adhesion interface, which is minimally proceeded by nature due to the polymerization inhibition derived from oxygen included in a wetting material, is easily proceeded. Therefore, the present composition exhibits high bond strength to a wetting material including oxygen. On the other hand, within the present composition, the aromatic sulfinate (d) dispersed in a second part does not dissolve in a mixed solution (i.e., a mixed solution of a first part and the second part) immediately after mixing the two parts but gradually dissolves in the mixed solution, and therefore, the radical generation reaction does not start for a time after mixing. Accordingly, a time necessary for an adhesion operation (i.e., a working time) can be secured. Furthermore, the present composition exhibits high bond durability. The reason is presumed as follows: Since the aromatic sulfinate is dissolved in the mixed solution after the mixing, even if an unreacted excessive portion of the aromatic sulfinate is exuded from a cured substance after curing, it does not produce a large space within the cured substance. This seems to be the reason why the present composition exhibits high mechanical strength of an adhesive layer and exhibits high bond durability when it is applied to a tooth crown repairing material such as a metal, porcelain, ceramics or a composite resin cured substance as compared with the redox-curing type nonaqueous curable composition disclosed in Patent Document 5, which uses, as a reducing agent, an inorganic metal salt such as sodium sulfite not dissolved in the composition but dispersed in a powder form after mixing. In the above description, dispersion of the aromatic sulfite or the inorganic metal salt means a state where at least a part of the aromatic sulfite or the inorganic metal salt is present in a solid form in the composition, and dissolution thereof means a state where it is mixed with a monomer in a liquid phase within the composition.

BEST MODE FOR CARRYING OUT THE INVENTION

The redox-curing type composition of the invention is a divided type composed of a first part and a second part. In the first part, at least an oxidizing agent (b) is dissolved in a first radical monomer including a radical monomer (a) having an acidic group and/or a hydrophilic group.

The radical monomer (a) having an acidic group and/or a hydrophilic group is polymerized through a radical polymerization reaction proceeded by a redox polymerization initiator. The radical monomer (a) having an acidic group and/or a hydrophilic group has an effect to dissolve an aromatic sulfinate (d) included in the second part described later.

An example of the radical monomer having an acidic group is a radical monomer having at least one acidic group, such as a phosphoric group, a pyrophosphoric group, a thiophosphoric group, a phosphonic group, a sulfonic group or a carboxylic group, and at least one radical polymeric group (i.e., a radical polymerizable unsaturated group), such as an acryloyl group, a methacryloyl group, a vinyl group or a styrene group. The radical monomer (a) having an acidic group has a decalcification function to improve the affinity with an adherend. Specific examples of the radical monomer (a) having an acidic group are as follows, in which a word "(meth)acryl" is used as a generic term for methacryl and acryl:

Examples of the monomer having a phosphoric group are 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts and ammonium salts of them.

Examples of the monomer having a pyrophosphoric group are bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl] pyrophosphate, bis[10-(meth)acryloyloxydecyl] pyrophosphate, and acid chlorides, alkali metal salts and ammonium salts of them.

Examples of the monomer having a thiophosphoric group are 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, 20-(meth)acryloyloxyicosyl dihydrogen thiophosphate, and acid chlorides, alkali metal salts and ammonium salts of them.

Examples of the monomer having a phosphonic group are 2-(meth)acryloyloxyethylphenyl phosphonate, 5-(meth)acryloyloxypentyl-3-phosphonopropyonate, 6-(meth)acryloyloxyhexyl-3-phosphonopropyonate, 10-(meth)acryloyloxydecyl-3-phosphonopropyonate, 6-(meth acryloyloxyhexyl-3-phosphonoacetate, 10-(meth)acryloyloxydecyl-3-phosphonoacetate, and acid chlorides, alkali metal salts and ammonium salts of them.

Examples of the monomer having a sulfonic group are 2-(meth)acrylamide-2-methylpropane sulfonate, styrene sulfonic acid and 2-sulfoethyl (meth)acrylate.

Examples of the monomer having a carboxylic group are a monomer having one carboxyl group in a molecule and a monomer having a plurality of carboxyl groups in a molecule.

Examples of the monomer having one carboxyl group in a molecule are (meth)acrylic acid, N-(meth)acryloyl glycine, N-(meth)acryloyl aspartate, N-(meth)acryloyl-5-amino-salicylic acid, O-(meth)acryloyl tyrosine, N-(meth)acryloyl tyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid and acid halides of them.

Examples of the monomer having a plurality of carboxyl groups in a molecule are 2-(meth)acryloyloxyethyl hydrogen succinate, 2-(meth)acryloyloxyethyl hydrogen phthalate, 2-(meth)acryloyloxyethyl hydrogen malate, 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate, 2-(meth)acryloyloxyethyl-3'-(meth)acryloyloxy-2'-(3,4-dicarboxybenzoyloxy)propyl succinate, and anhydrides and acid halides of them.

Among the aforementioned radical monomers having an acidic group, 10-(meth)acryloyloxydecyl dihydrogen phosphate, 1,3-di(meth)acryloyloxypropyl dihydrogen phosphate, 2-(meth)acryloyloxyethyl dihydrogen phosphate, 4-(meth)acryloyloxyethyl trimellitate anhydride, 4-(meth)acryloyloxyethyl trimellitate, 2-(meth)acrylamide-2-methylpropane sulfonate and 11-(meth)acryloyloxyundecane-1,1-dicarboxylic acid are preferably used because they exhibit high bond strength when used as a dental adhesive and a working time can be adjusted with the aromatic sulfinate (d) included in the second part allowed to dissolve in a desired time in mixing the first part and the second part. One of these radical monomers having an acidic group may be singly used or a plurality of them may be used together.

An example of the radical monomer having a hydrophilic group is a radical monomer having a hydroxyl group. Specific examples of the radical monomer having a hydroxyl group are (meth)acrylate having a hydroxyl group such as 2-hydroxyethyl (meth)acrylate, 2- or 3-hydroxypropyl(meth)acrylate, 4-hydroxybutyl(meth)acrylate, 5-hydroxypentyl (meth)acrylate, 6-hydroxyhexyl(meth)acrylate, 10-hydroxydecyl (meth)acrylate, 1,2- or 1,3- or 2,3-dihydroxypropane (meth)acrylate, glycerol di(meth)acrylate, 1,2-bis[3-(meth)acryloyloxy-2-hydroxypropyloxy]ethane, diethylene glycol mono(meth)acrylate, triethylene glycol mono(meth)acrylate, tetraethylene glycol mono(meth)acrylate, pentamethylene glycol mono(meth)acrylate, polyethylene glycol mono(meth)acrylate, dipropylene glycol mono (meth)acrylate or polypropylene glycol mono(meth)acrylate; (meth)acrylamide having a hydroxyl group such as N-methylol (meth)acrylamide, N-(2-hydroxyethyl) (meth)acrylamide, N-(3-hydroxypropyl) (meth)acrylamide, N-(4-hydroxybutyl) (meth)acrylamide, N-(5-hydroxypentyl) (meth) acrylamide, N-(6-hydroxyhexyl) (meth)acrylamide, N-(10-hydroxydecyl) (meth)acrylamide, N-(meth)acryloyl-1,2-dihydroxypropylamine, N-(meth)acryloyl-1,3-dihydroxypropylamine or N-(meth)acryloyl-2,3-dihydroxypropylamine; and an addition product of glycidyl (meth)acrylate (GMA) and aliphatic or aromatic polyol (including phenol), such as 2-hydroxy-3-phenoxypropyl(meth)acrylate, 2-hydroxy-3-naphthoxypropyl (meth)acrylate or bisphenol A diglycidyl(meth)acrylate.

Among the radical monomers having a hydroxyl group, bisphenol A diglycidyl (meth)acrylate, 2-hydroxyethyl (meth)acrylate, glycerol di(meth)acrylate and 1,2-bis[3-(meth)acryloyloxy-2-hydroxypropyloxy]ethane are preferably used because they exhibit high affinity with dentine and high bond strength when used as a dental adhesive and a working time can be adjusted with the aromatic sulfinate (d) included in the second part allowed to dissolve in a desired time in mixing the first part and the second part. One of these radical monomers having a hydroxyl group may be singly used or a plurality of them may be used together.

The first radical monomer includes the radical monomer (a) having an acidic group and/or a hydrophilic group. The content in the first radical monomer of the radical monomer (a) having an acidic group and/or a hydrophilic group is preferably 1 through 100 wt % because a working time can be adjusted with the aromatic sulfinate (d) included in the second part allowed to dissolve in a desired time in mixing the first part and the second part, and is more preferably 3 through 85 wt % and most preferably 5 through 70 wt %. When the content of the radical monomer (a) having an acidic group and/or a hydrophilic group is less than 1 wt %, the bond strength of a resultant composition to a wetting material may be low.

One of the aforementioned radical monomers (a) having an acidic group and/or a hydrophilic group may be singly used, but any of the radical monomers having an acidic group and any of the radical monomers having a hydrophilic group are preferably used together because high bond strength can be thus attained when used as a dental adhesive. The ratio between these radical monomers used together is not particularly specified and may be appropriately set in consideration of the curability of a resultant composition and the like.

The first radical monomer may include, in addition to the radical monomer (a) having an acidic group and/or a hydrophilic group, a radical monomer having neither an acidic group nor a hydrophilic group as far as the effects of the invention are not spoiled. Specific examples of the radical monomer having neither an acidic group nor a hydrophilic group are those described below as examples of a radical monomer (c) having neither an acidic group nor a hydrophilic group to be included in a second radical monomer.

Examples of the oxidizing agent (b) to be dissolved in the first radical monomer are an organic peroxide, an azo compound, an organic boron compound, an inorganic peroxide and a metal salt. Examples of the organic peroxide are diacyl peroxides, peroxy esters, dialkyl peroxides, peroxy ketals, ketone peroxides and hydroperoxides. Specific examples of the diacyl peroxides are benzoyl peroxide, 2,4-dichlorobenzoyl peroxide and m-toluoyl peroxide. Specific examples of the peroxy esters are t-butyl peroxybenzoate, bis-t-butyl peroxyisophthalate, 2,5-dimethyl-2,5-bis(benzoylperoxy)hexane, t-butylperoxy-2-ethylhexanoate and t-butylperoxy isopropyl carbonate. Specific examples of the dialkyl peroxides are dicumyl peroxide, di-t-butyl peroxide and lauroyl peroxide. Specific examples of the peroxy ketals are 1,1-bis(t-butylperoxy)3,3,5-trimethylcyclohexane, 1,1-bis(t-butylperoxy)cyclohexane and 1,1-bis(t-hexylperoxy)cyclohexane. Specific examples of the ketone peroxides are methyl ethyl ketone peroxide, cyclohexanone peroxide and methyl acetoacetate peroxide. Specific examples of the hydroperoxides are t-butyl hydroperoxide, cumene hydroperoxide and p-diisopropyl benzene peroxide. Examples of the azo compound are azobisisobutyronitrile and azobisisobutyrovaleronitrile. Examples of the organic boron compound are trialkyl boron and a partial oxide of trialkyl boron. Examples of the inorganic peroxide are sodium peroxide, potassium peroxide, aluminum peroxide and ammonium peroxide. Examples of the metal salt are a salt of cobalt (III), a salt of iron (III), a salt of copper (II) and a salt of permanganate anion.

The content of the oxidizing agent (b) in the first part is preferably 0.01 through 10 parts by weight based on 100 parts by weight of the first radical monomer from the viewpoint of the curability of a resultant composition. When the content is less than 0.01 part by weight, it is apprehended that the mechanical strength of a cured substance may be low and that the bond strength may be low. On the other hand, also when the content exceeds 10 parts by weight, it is apprehended that the bond strength may be low.

In the second part, at least the aromatic sulfinate (d) is dispersed in the second radical monomer including the radical monomer (c) having neither an acidic group nor a hydrophilic group.

The radical monomer (c) having neither an acidic group nor a hydrophilic group is polymerized through a radical polymerization reaction proceeded by a redox polymerization initiator.

The monomer used in the second part is limited to the monomer having neither an acidic group nor a hydrophilic group for the following reason: The aromatic sulfinate (d) is easily dissolved in a monomer having an acidic group or a hydrophilic group, and therefore, the aromatic sulfinate (d) cannot be dispersed in the second part but a radical generation reaction is proceeded immediately after mixing the first part and the second part, and hence, a time for an adhesion operation cannot be secured.

Examples of the radical monomer (c) having neither an acidic group nor a hydrophilic group are an ester of carboxylic acid such as α-cyanoacrylic acid, (meth)acrylic acid, α-halogenated acrylate, crotonic acid, cinnamic acid, sorbic acid, maleic acid or itaconic acid, (meth)acrylamide and a derivative thereof, vinyl esters, vinyl ethers, a mono-N-vinyl derivative and a styrene derivative. Among them, (meth) acrylic ester is preferred.

Specific examples of the radical monomer (c) having neither an acidic group nor a hydrophilic group are described below. In the following, a monomer having one olefin double bond is mentioned as a monofunctional monomer, a monomer having two olefin double bonds is mentioned as a bifunctional monomer and a monomer having three or more olefin double bonds is mentioned as a tri- or multifunctional monomer:

Monofunctional Monomers:
methyl(meth)acrylate, ethyl(meth)acrylate, propyl(meth) acrylate, isopropyl (meth)acrylate, butyl(meth)acrylate, isobutyl(meth)acrylate, benzyl(meth)acrylate, lauryl (meth)acrylate, 2,3-dibromopropyl(meth)acrylate, 3-(meth)acryloyloxypropyltrimethoxysilane, 11-(meth) acryloyloxyundecyltrimethoxysilane and (meth)acrylamide Bifunctional Monomers:
ethylene glycol di(meth)acrylate, triethylene glycol di(meth) acrylate, propylene glycol di(meth)acrylate, polyethylene glycol di(meth)acrylate, neopentyl glycol di(meth)acrylate, 1,6-hexanediol di(meth)acrylate, 1,10-decanediol di(meth)acrylate, 2,2-bis[4-(meth)acryloyloxyethoxyphenyl]propane, 2,2-bis[4-(meth)acryloyloxypolyethoxyphenyl]propane and [2,2,4-trimethylhexamethylene bis(2-carbamoyloxyethyl)]di(meth)acrylate Tri- or Multifunctional Monomers:
trimethylolpropane tri(meth)acrylate, trimethylolethane tri (meth)acrylate, N,N'-(2,2,4-trimethylhexamethylene) bis [2-(aminocarboxy)propane-1,3-diol]tetra(meth)acrylate and 1,7-diacryloyloxy-2,2,6,6-tetra(meth)acryloyloxymethyl-4-oxyheptane Among the aforementioned radical monomers (c) having neither an acidic group nor a hydrophilic group, 2,2-bis[4-(meth)acryloyloxypolyethoxyphenyl]propane, neopentyl glycol di(meth)acrylate, triethylene glycol di(meth)acrylate, [2,2,4-trimethylhexamethylene]bis(2-carbamoyloxyethyl) di(meth)acrylate, N,N'-(2,2,4-trimethylhexamethylene) bis [2-(aminocarboxy)propane-1,3-diol]tetra(meth)acrylate and 1,10-decanediol di(meth)acrylate are preferred from the viewpoint of the mechanical strength and the handling property in use as a dental adhesive.

One of the radical monomers (c) having neither an acidic group nor a hydrophilic group may be singly used but a plurality of them are preferably used together. When a plurality of them are used together, an appropriate combination is employed in consideration of the mechanical strength, the handling property and the transparency of a resultant composition.

The second radical monomer includes the radical monomer (c) having neither an acidic group nor a hydrophilic group. The content in the second radical monomer of the radical monomer (c) having neither an acidic group nor a hydrophilic group is preferably 60 through 100 wt %, more preferably 65 through 100 wt % and most preferably 70 through 100 wt %. When the content is less than 40 wt %, a time usable for performing an adhesion operation with a resultant composition (namely, the working time) may be short.

The second radical monomer may include, in addition to the radical monomer (c) having nether an acidic group nor a hydrophilic group, a radical monomer having a hydrophilic group as far as the effects of the invention are not spoiled.

Specific examples of the radical monomer having a hydrophilic group are those mentioned as the specific examples of the radical monomer (a) to be included in the radical monomer of the first part.

The aromatic sulfinate (d) dispersed in the second radical monomer is a reducing agent component of the redox polymerization initiator. Examples of the aromatic sulfinate (d) are lithium salt, sodium salt, potassium salt, rubidium salt, cesium salt, magnesium salt, calcium salt, strontium salt, iron salt, copper salt, zinc salt, ammonium salt, tetramethyl ammonium salt and tetraethyl ammonium salt of benzenesulfinic acid, p-toluenesulfinic acid, o-toluenesulfinic acid, ethylbenzenesulfinic acid, decylbenzenesulfinic acid, dodecylbenzenesulfinic acid, 2,4,6-trimethylbenzenesulfinic acid, 2,4,6-triisopropylbenzenesulfinic acid, chlorobenzenesulfinic acid, naphthalenesulfinic acid or the like. Among them, lithium salt, sodium salt, potassium salt, magnesium salt or calcium salt of 2,4,6-trimethylbenzenesulfinic acid and 2,4,6-triisopropylbenzenesulfinic acid are preferred from the viewpoint of the curability and the storage stability of a resultant composition, and lithium salt, sodium salt, potassium salt, magnesium salt or calcium salt of 2,4,6-triisopropylbenzenesulfinic acid is more preferred.

The aromatic sulfinate (d) preferably has solubility in water at an ordinary temperature (of 25° C.) of 1 mg/100 mL or more. When the solubility is lower than 1 mg/100 mL, in the application of the present composition to a wetting material, the aromatic sulfinate (d) is not sufficiently dissolved in water present on the surface of the wetting material, and as a result, the polymerization curability on the adhesion interface cannot be improved.

The aromatic sulfinate (d) has an average particle diameter preferably of 500 μm or less and more preferably of 100 μm or less because it is easily precipitated when the particle diameter is large. When the average particle diameter is too small, however, the specific surface area of the powder may be so large that the handling property of the second part may be degraded, and therefore, the average particle diameter is preferably 0.01 μm or more. Specifically, the average particle diameter of the aromatic sulfinate (d) is preferably 0.01 through 500 μm and more preferably 0.01 through 100 μm.

The aromatic sulfinate (d) may be in any of various shapes including a spherical shape, a needle shape, a plate shape and a crushed shape, and its shape is not particularly specified. The aromatic sulfinate (d) may be prepared by any of known methods including a grinding method and a freeze-drying method.

The content of the aromatic sulfinate (d) in the second part is preferably 0.1 through 20 parts by weight, more preferably 0.2 through 15 parts by weight and most preferably 0.5 through 10 parts by weight based on 100 parts by weight of the second radical monomer. When the content is less than 0.1 part by weight, it is apprehended that the bond strength of a resultant composition to a wetting material may be low. On the other hand, when the content exceeds 20 parts by weight, it is apprehended that the handling property of a resultant second part may be degraded.

In order to adjust the curing time of the present composition, the second part may further include, as a reducing agent component of the redox polymerization initiator, any of known reducing compounds such as aliphatic amine and aromatic amine. Attention should be paid, however, because the working time may be largely reduced when such a reducing compound is excessively included.

Examples of the aliphatic amine are primary aliphatic amine such as n-butylamine, n-hexylamine or n-octylamine; secondary aliphatic amine such as diisopropylamine, dibutylamine or N-methyl diethanolamine; and tertiary aliphatic amine such as N-methyl diethanolamine, N-ethyl diethanolamine, N-n-butyl diethanolamine, N-lauryl diethanolamine, 2-(dimethylamino)ethyl(meth)acrylate, N-methyl diethanolamine di(meth)acrylate, N-ethyl diethanolamine di(meth) acrylate, triethanolamine tri(meth)acrylate, triethanolamine, trimethylamine, triethylamine or tributylamine. Among them, tertiary aliphatic amine is preferred, and N-methyl diethanolamine and triethanolamine are particularly preferred from the viewpoint of the curability and the storage stability of a resultant composition.

Examples of the aromatic amine are N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethyl aniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, 4-N,N-dimethylaminobenzoic acid ethyl ester, 4-N,N-dimethylaminobenzoic acid methyl ester, N,N-dimethylaminobenzoic acid n-butoxyethyl ester, 4-N,N-dimethylaminobenzoic acid 2-[(meth)acryloyloxy]ethyl ester, 4-N,N-dimethylaminobenzophenone and butyl 4-dimethylaminobenzoate. Among them, N,N-di(2-hydroxyethyl)-p-toluidine, 4-N,N-dimethylaminobenzoic acid ethyl ester, N,N-dimethylaminobenzoic acid n-butoxyethyl ester and 4-N,N-dimethylaminobenzophenone are preferably used because a resultant composition can attain high curability. One of the aforementioned aliphatic amine or the aromatic amine may be singly used or a plurality of them may be used together. Also, aliphatic amine and aromatic amine may be used together if necessary.

In order to prepare the present composition as a dual cure type composition in which polymerization is started also through irradiation with light, another known photopolymerization initiator may be included in addition to the redox polymerization initiator. Examples of the known photopolymerization initiator are α-diketones, ketals, thioxanthones, acyl phosphine oxides and α-aminoacetophenones. The photopolymerization initiator may be included in both of or one of the first part and the second part.

Specific examples of the α-diketones are camphorquinone, benzyl and 2,3-pentanedione.

Specific examples of the ketals are benzyl dimethylketal and benzyl diethylketal.

Specific examples of the thioxanthones are 2-chlorothioxanthone and 2,4-diethylthioxantone.

Specific examples of the acyl phosphine oxides are 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphine oxide, 2,4,6-trimethylbenzoylethoxyphenylphosphine oxide and a water-soluble acyl phosphine oxide compound disclosed in Japanese Laid-Open Patent Publication No. 3-57916.

Specific examples of the α-aminoacetophenones are 2-benzyl-2-dimethylamino-1-(4-morpholinophenyl)-butanone-1,2-benzyl-2-diethylamino-1-(4-morpholinophenyl)-butanone-1,2-benzyl-2-dimethylamino-1-(4-morpholinophenyl)-propanone-1,2-benzyl-2-diethylamino-1-(4-morpholinophenyl)-propanone-1,2-benzyl-2-dimethylamino-1-(4-morpholinophenyl)-pentanone-1 and 2-benzyl-2-diethylamino-1-(4-morpholinophenyl)-pentanone-1.

One of these photopolymerization initiators may be singly used or a plurality of them may be used together. The content of the photopolymerization initiator is preferably 0.01 through 10 parts by weight and more preferably 0.1 through 5 parts by weight based on 100 parts by weight of a sum of the first radical monomer and the second radical monomer.

Furthermore, in order to improve the photo-setting property, the photopolymerization initiator may be used together with a polymerization promoter such as aliphatic amine, aromatic amine, an aldehyde or a thiol compound.

Specific examples of the aliphatic amine and the aromatic amine are the same as those mentioned above as the examples of the aliphatic amine and the aromatic amine.

Specific examples of the aldehyde are dimethylaminobenzaldehyde and terephthalaldehyde.

Specific examples of the thiol compound are 2-mercaptobenzoxazole, decane thiol, 3-mercaptopropyltrimethoxysilane and thiobenzoic acid.

One of these polymerization promoters may be singly used or a plurality of them may be used together. Attention should be paid, however, because when the polymerization promoter is excessively included, the redox polymerization is excessively proceeded so as to largely reduce the working time of a resultant composition.

The present composition may further include a glass filler for improving the mechanical strength attained after curing. As the glass filler to be included, one of or both of an ion unexchangeable glass filler and an ion exchangeable glass filler may be used. Examples of the ion unexchangeable glass filler are an inorganic filler, an organic filler and a composite filler of them. Examples of the inorganic filler are silica; a mineral including silica as a base material and including kaoline, clay, mica or the like; ceramics including silica as a base material and including $Al_2O_3$, $B_2O_3$, $TiO_2$, $ZrO_2$, $BaO$, $La_2O_3$, $SrO_2$, $CaO$, $P_2O_5$ or the like; and glass such as lanthanum glass, barium glass or strontium glass. Alternatively, quartz, hydroxylapatite, alumina, titanium oxide, ytterbium oxide, ytterbium fluoride, zirconia, barium sulfate or the like may be used as the inorganic filler. Examples of the organic filler are organic resins such as polymethyl methacrylate, polyamide, polystyrene, polyvinyl chloride, polychloroprene rubber, nitrile rubber and styrene-butadiene rubber. Examples of the composite filler are one obtained by dispersing an ion unexchangeable glass filler in any of the organic resins and one obtained by coating the surface of an ion unexchangeable filler with any of the organic resins. An example of the ion exchangeable glass filler is fluoroaluminosilicate glass including a cation exchangeable element (such as strontium, calcium, zinc, aluminum, iron or zirconium) having a valence of two or more that can be reacted with a radical monomer having an acidic group (which fluoroaluminosilicate glass is, for example, calcium fluoroaluminosilicate glass, strontium fluoroaluminosilicate glass, barium fluoroaluminosilicate glass or strontium calcium fluoroaluminosilicate glass). Such a filler may be subjected, before use, to a surface treatment with a known coupling agent such as a silane coupling agent if necessary. Examples of the coupling agent are vinyl trimethoxysilane, vinyl triethoxysilane, vinyl trichlorosilane, vinyl tri(β-methoxyethoxy)silane, γ-(meth)acryloyloxypropyl trimethoxysilane, γ-glycidoxypropyl trimethoxysilane, γ-mercaptopropyl trimethoxysilane and γ-aminopropyl triethoxysilane.

In the case where the present composition is applied to a biological hard tissue, and more particularly, to a tooth, the present composition may further include a known water-soluble fluoride compound that releases fluorine ions in an amount not spoiling the adhesiveness. Examples of the water-soluble fluoride compound are lithium fluoride, sodium fluoride, potassium fluoride, rubidium fluoride, cesium fluoride, beryllium fluoride, magnesium fluoride, calcium fluoride, strontium fluoride, barium fluoride, zinc fluoride, aluminum fluoride, manganese fluoride, copper fluoride, lead fluoride, silver fluoride, antimony fluoride, cobalt fluoride, bismuth fluoride, beryllium fluoride, tin fluoride, diammine silver fluoride, sodium monofluorophosphate, titanium potassium fluoride, stannate fluoride and fluorosilicate. One of these water-soluble fluoride compounds may be singly used or a plurality of them may be used together. When a water-soluble fluoride compound is included, it is preferably added after forming it into fine particles by a method described in, for example, Japanese Laid-Open Patent Publication No. 2-258602 or after coating it with polysiloxane by a method described in, for example, Japanese Laid-Open Patent Publication No. 10-36116 before the addition.

The present composition may include any of conventional stabilizers, photopolymerization initiators, dyes and pigments.

The packaging form of the present composition is a divided type composed of the first part and the second part. If it is packaged in one part, the aromatic sulfinate (d) is dissolved in the radical monomer (a) having an acidic group and/or a hydrophilic group, and the dissolved aromatic sulfinate (d) is reacted with the oxidizing agent (b) to be decomposed during the storage, resulting in reducing the amount of radicals to be generated.

The weight ratio for mixing the first part and the second part is preferably 1:10 through 5:1 from the viewpoint of the curability of a resultant composition and the time usable for an adhesion operation (i.e., the working time).

It is assumed that the present composition is applied to a wetting material in the following description: Since the present composition is packaged dividedly as the first part and the second part, the first part and the second part are mixed into a mixture before use and the mixture is applied to a wetting material. The curing reaction speed is increased on the adhesion interface due to contact between the mixture and moisture present on the surface of the wetting material, and when the curing reaction is completed, the present composition and the wetting material are adhered to each other. Application to a tooth will be described in more detail. When a tooth cavity is to be filled for repair, the tooth cavity is cleaned by a general method, and the mixture of the present composition is filled in the tooth cavity. When a prosthesis such as a crown or an inlay is cemented, after an adherend of an abutment tooth or a tooth cavity and an adherend of the prosthesis are cleaned, the mixture of the present composition is applied to at least one of the adherend of the abutment tooth or the tooth cavity and the adherend of the prosthesis for cementing them. Before applying the present composition to a tooth surface, the tooth surface may be subjected to a known pretreatment such as etching with an acidic aqueous solution, modification with a primer or simultaneous etching/modification with a primer capable of etching.

EMBODIMENTS

Preferred embodiments of the invention will now be described in more detail. It is noted that the present invention is not limited to the embodiments described below. The following abbreviated words are used in the description of the embodiments:

MDP: 10-methacryloyloxydecyl dihydrogen phosphate
D-2.6E: 2,2-bis(methacryloyloxypolyethoxyphenyl)propane
NPG: neopentyl glycol dimethacrylate
Bis-GMA: bisphenol A diglycidyl methacrylate
HEMA: 2-hydroxyethyl methacrylate
TPBSS: sodium 2,4,6-triisopropylbenzenesulfinate
BPO: benzoyl peroxide
DEPT: N,N-diethanol-p-toluidine
TMDPO: 2,4,6-trimethylbenzoyldiphenylphosphine oxide
BHT: dibutyl hydroxyl toluene
R972: silica (manufactured by Nippon Aerosil, trade name: "Aerosil R972")

Embodiments 1 Through 8

First parts and second parts respectively having compositions listed in Table 1 were prepared, so as to fabricate divided redox-curing type compositions (present compositions) each composed of a first part and a second part in the weight ratio of 1:1. Each first part was prepared by mixing components other than a silanated quartz filler and R972, stirring the resultant so as to obtain a homogeneous solution, mixing the solution with a silanated quartz filler and R972, and degassing the resultant. Also, each second part was prepared by mixing components other than TPBSS, a silanated quartz filler and R972, stirring the resultant so as to obtain a homogeneous solution, mixing the solution with TPBSS, a silanated quartz filler and R972, and degassing the resultant. The TPBSS was dispersed in a powder form in the second part. With respect to each of the divided redox-curing type compositions, the working time, the tensile bond strength and the bond durability on porcelain and the tensile bond strength and the bond durability on gold alloy were examined by methods described below. Also, with respect to each of the divided redox-curing type compositions of Embodiments 2 trough 4, the tensile bond strength and the bond durability on a dentine (a bovine dentine) were also examined by a method described below.

Comparative Examples 1 Through 4

Divided redox-curing type compositions (comparative compositions) each composed of a first part and a second part, whose compositions are listed in Table 2, in the weight ratio of 1:1 were fabricated in the same manner as in Embodiments 2 through 4 except that a sodium sulfite powder was used instead of the TPBSS in the preparation of each second part (as Comparative Examples 1 through 3). Also, a divided redox-curing type composition (comparative composition) composed of a first part and a second part, whose compositions are listed in Table 2, in the weight ratio of 1:1 was fabricated with the TPBSS dissolved in a monomer in the second part (as Comparative Example 4). With respect to each of the divided redox-curing type compositions, the working time, the tensile bond strength and the bond durability on porcelain, the tensile bond strength and the bond durability on gold alloy and the tensile bond strength and the bond durability on a dentine (a bovine dentine) were examined by the methods described below.

[Working Time]

A first part and a second part were filled in the weight ratio of 1:1 respectively in a pair of vessels arranged in parallel (each with a volume of 5 ml, manufactured by MIXPAC SYSTEMS AG, product code "SDL005-01052"), the pastes filled in the respective vessels were extruded into a mixing section of a mixer (manufactured by MIXPAC SYSTEMS AG, product code "ML2.5-08-S") for mixing the two parts in the mixing section, and approximately 30 mg of the thus obtained mixture was discharged onto a slide glass for a microscope. After a precedent time elapsed after starting mixing, another slide glass for a microscope was pressed against the mixture so as to apply shear force, and it was visually checked whether or not there was an inhomogeneous portion in the mixture. This check was repeatedly performed with the time from the start of mixing to the application of the shear force extended by 10 seconds each until an inhomogeneous portion was formed. Since a time when an inhomogeneous portion is formed corresponds to a time when curing starts, the time from the start of mixing to the formation of an inhomogeneous portion was regarded as the working time (the time usable for an adhesion operation) of a tested divided redox-curing type composition. The results are listed in Table 3 below.

[Tensile Bond Strength and Bond Durability on Porcelain or Gold Alloy]

The surfaces of a porcelain block (manufactured by Vita, brand name "Celay") and a cubic gold alloy cast with a side of 1 cm (manufactured by GC Corporation, brand name "Casting Gold M. C. type IV") were polished for smoothing with #1000 silicon carbide paper in running water, and water remaining on the surfaces were air blown for drying. An adhesive tape having a thickness of approximately 150 μm and having a hole with a diameter of 5 mm was adhered onto each of the smooth surfaces obtained after drying for restraining an adhesion area.

The first part and the second part of each divided redox-curing type composition were mixed in the weight ratio of 1:1, thereby preparing a cement composition. The cement composition was built up on one end face (a circular end face) of a stainless steel cylindrical bar (with a diameter of 7 mm and a length of 2.5 mm), the end face having the cement composition was placed on each smooth surface (adherend) restrained in the hole so that the center of the hole and the center of the stainless steel cylindrical bar could substantially accord with each other, and the stainless steel bar was vertically pressed against the smooth surface for adhesion, thereby preparing a test sample. Ten test samples were thus prepared with respect to each of the porcelain block and the gold alloy cast.

After removing an excessive portion of the cement composition forced out from the circumference of the stainless steel cylindrical bar in pressing, the test sample was allowed to stand at room temperature for 30 minutes and then dipped in distilled water. After dipping in distilled water, the test sample was allowed to stand in a thermostat kept at 37° C. for 24 hours. Five of the ten test samples were used for checking the tensile bond strength after the standing at 37° C. for 24 hours. This tensile bond strength corresponds to bond strength attained at the initial stage of the adhesion. Furthermore, the other five test samples were allowed to stand in a thermostat kept at 70° C. for 10 days after the standing at 37° C. for 24 hours and then were used for checking the tensile bond strength. This tensile bond strength corresponds to bond durability. The tensile bond strength was measured with a universal testing machine (manufactured by Shimadzu Corporation) with a crosshead speed set to 2 mm/min. The results are listed in Table 3 below. The tensile bond strength obtained after the standing at 37° C. for 24 hours and the tensile bond strength obtained after the standing at 70° C. for 10 days listed in Table 3 are both averages of values obtained by the five test samples.

[Tensile Bond Strength and Bond Durability on Bovine Dentine]

A labial surface of a bovine mandibular incisor was polished with silicon carbide paper in running water, so as to expose a smooth dentine surface. The exposed smooth dentine surface was further polished with #1000 silicon carbide paper in running water. After the polishing, water remaining on the surface was air blown for drying. After drying, an adhesive tape having a thickness of approximately 150 μm and having a hole with a diameter of 3 mm was adhered onto the smooth surface for restraining an adhesion area.

The first part and the second part of each divided redox-curing type composition were mixed in the weight ratio of 1:1, thereby preparing a cement composition. The cement composition was built up on one end face (a circular end face) of a stainless steel cylindrical bar (with a diameter of 7 mm and a length of 2.5 mm), the end face having the cement composition was placed on the smooth surface (adherend) restrained in the hole so that the center of the hole and the center of the stainless steel cylindrical bar could substantially accord with each other, and the stainless steel bar was vertically pressed against the smooth surface, thereby preparing a test sample. Ten test samples were thus prepared.

After removing an excessive portion of the cement composition forced out from the circumference of the stainless steel cylindrical bar in pressing, the test sample was allowed to stand at room temperature for 30 minutes and then dipped in distilled water. After dipping in distilled water, the test sample was allowed to stand in a thermostat kept at 37° C. for 24 hours. Five of the ten test samples were used for checking the tensile bond strength after the standing at 37° C. for 24 hours. This tensile bond strength corresponds to bond strength attained at the initial stage of the adhesion. Furthermore, the other five test samples were allowed to stand at 37° C. for 24 hours and then subjected to load through 4000 thermal cycles (which thermal cycles are hereinafter referred to as "TC4000") in each cycle of which each sample was dipped in cool water of 4° C. and warm water of 60° C. for 1 minute each, and then, the tensile bond strength was checked. This tensile bond strength corresponds to bond durability. The tensile bond strength was measured with a universal testing machine (manufactured by Shimadzu Corporation) with a crosshead speed set to 2 mm/min. The results are listed in Table 4 below. The tensile bond strength obtained after the standing at 37° C. for 24 hours and the tensile bond strength obtained after the TC4000 listed in Table 4 are both averages of values obtained by the five test samples.

TABLE 1

| Components | First part (parts by weight) | Second part (parts by weight) | | | | | | | |
|---|---|---|---|---|---|---|---|---|---|
| | | Emb. 1 | Emb. 2 | Emb. 3 | Emb. 4 | Emb. 5 | Emb. 6 | Emb. 7 | Emb. 8 |
| MDP | 20 | — | — | — | — | — | — | — | — |
| D-2.6E | 40 | 60 | 60 | 60 | 60 | 60 | 60 | 60 | 60 |
| NPG | 20 | 40 | 40 | 40 | 40 | 35 | 30 | 20 | 10 |
| Bis-GMA | 20 | — | — | — | — | 5 | 10 | 20 | 30 |
| TPBSS | — | 0.2 | 1 | 3 | 5 | 3 | 3 | 3 | 3 |
| BPO | 2 | — | — | — | — | — | — | — | — |
| DEPT | — | 0.4 | 0.4 | 0.4 | 0.4 | 0.4 | 0.4 | 0.4 | 0.4 |
| TMDPO | — | 0.5 | 0.5 | 0.5 | 0.5 | 0.5 | 0.5 | 0.5 | 0.5 |
| BHT | 0.05 | 0.05 | 0.05 | 0.05 | 0.05 | 0.05 | 0.05 | 0.05 | 0.05 |
| Silanated quartz filler | 220 | 220 | 220 | 220 | 220 | 220 | 220 | 220 | 220 |
| R972 | 15 | 15 | 15 | 15 | 15 | 15 | 15 | 15 | 15 |

TABLE 2

| Components | First part (parts by weight) | Second part (parts by weight) | | | |
|---|---|---|---|---|---|
| | | Com. Ex. 1 | Com. Ex. 2 | Com. Ex. 3 | Com. Ex. 4 |
| MDP | 20 | — | — | — | — |
| D-2.6E | 40 | 60 | 60 | 60 | 50 |
| NPG | 20 | 40 | 40 | 40 | — |
| Bis-GMA | 20 | — | — | — | — |
| HEMA | — | — | — | — | 50 |
| TPBSS | — | — | — | — | 3 |
| Sodium sulfite powder | — | 1 | 3 | 5 | — |
| BPO | 2 | — | — | — | — |
| DEPT | — | 0.4 | 0.4 | 0.4 | 0.4 |
| TMDPO | — | 0.5 | 0.5 | 0.5 | 0.5 |
| BHT | 0.05 | 0.05 | 0.05 | 0.05 | 0.05 |
| Silanated quartz filler | 220 | 220 | 220 | 220 | 220 |
| R972 (silica particles) | 15 | 15 | 15 | 15 | 15 |

TABLE 3

| | | Tensile bond strength (MPa) | | | |
|---|---|---|---|---|---|
| | | Porcelain | | Gold alloy | |
| | Working time | after 1 day at 37° C. | after 10 days at 70° C. | after 1 day at 37° | after 10 days at 70° C. |
| Emb. 1 | over 5 min. | 20.5 | 19.9 | 22.5 | 20.1 |
| Emb. 2 | 4 min. 40 sec. | 21.8 | 20.9 | 23.4 | 20.7 |
| Emb. 3 | 3 min. 20 sec. | 21.0 | 19.1 | 24.7 | 19.5 |
| Emb. 4 | 3 min. 20 sec. | 19.9 | 18.5 | 23.2 | 18.8 |
| Emb. 5 | 3 min. 00 sec. | 21.4 | 19.6 | 24.5 | 20.2 |
| Emb. 6 | 2 min. 40 sec. | 19.6 | 18.0 | 22.1 | 18.5 |
| Emb. 7 | 2 min. 20 sec. | 19.7 | 18.2 | 21.6 | 19.0 |
| Emb. 8 | 1 min. 40 sec. | 20.5 | 18.9 | 22.3 | 18.7 |
| Com. Ex. 1 | over 5 min. | 20.3 | 12.8 | 18.9 | 13.5 |
| Com. Ex. 2 | over 5 min. | 17.6 | 7.0 | 16.2 | 10.5 |
| Com. Ex. 3 | over 5 min. | 16.6 | 3.2 | 15.8 | 4.1 |
| Com. Ex. 4 | 50 sec. | Not measured | Not measured | Not measured | Not measured |

TABLE 4

| | Tensile Bond Strength (MPa) Dentine | |
|---|---|---|
| | after 1 day at 37° C. | after TC4000 |
| Embodiment 2 | 6.4 | 5.6 |
| Embodiment 3 | 7.5 | 6.4 |
| Embodiment 4 | 7.1 | 6.1 |
| Comparative Example 1 | 4.5 | 4.0 |
| Comparative Example 2 | 6.0 | 4.7 |
| Comparative Example 3 | 6.2 | 5.0 |

It is understood from Table 3 that the cement compositions of the present compositions (of Embodiments 1 through 8) are better at the bond durability on porcelain and gold alloy, which are generally used as crown repairing materials, than the cement compositions of the comparative compositions (of Comparative Examples 1 through 3). Furthermore, although many of the cement compositions of the present compositions have a shorter working time than the cement compositions of the comparative compositions (of Comparative Examples 1 through 3), the shortest working time is 1 minute 40 seconds, which causes no practical problem. The cement composition of the comparative composition (of Comparative Example 4) in which the TPBSS was dissolved in the monomer during the preparation of the second part has a working time as short as less than 1 minute. This is probably because the radical generation reaction was started immediately after mixing the first part and the second part.

It is understood from Table 4 that the cement compositions of the present compositions (of Embodiments 2 through 4) using the aromatic sulfinate exhibits bond durability substantially equivalent to that of the cement compositions of the comparative compositions (of Comparative Examples 1 through 3) using the sodium sulfite powder when they are applied to a dentine.

The invention claimed is:

1. A divided redox-curing type composition comprising:
   a first part in which at least an oxidizing agent (b) is dissolved in a first radical monomer including a radical monomer (a) having an acidic group and/or a hydrophilic group; and
   a second part in which at least an aromatic sulfinate (d) is dispersed in a powder form in a second radical monomer comprising at least one radical monomer (c) having neither an acidic group nor a hydrophilic group selected from the group consisting of 2,2-bis[4-(meth)acryloyloxypolyethoxyphenyl]propane, neopentyl glycol di(meth)acrylate, N,N'-(2,2,4-trimethylhexamethylene) bis[2-(aminocarboxy)propane-1,3-diol]tetra(meth) acrylate and 1,10-decanediol di(meth)acrylate.

2. The divided redox-curing type composition according to claim 1,
   wherein a content of the radical monomer (a) having an acidic group and/or a hydrophilic group in the first radical monomer is from 1 to 100 wt %, a content of the radical monomer (c) having neither an acidic group nor a hydrophilic group in the second radical monomer is from 60 to 100 wt %, a content of the oxidizing agent (b) in the first part is from 0.01 to 10 parts by weight based on 100 parts by weight of the first radical monomer, a content of the aromatic sulfinate (d) in the second part is from 0.1 to 20 parts by weight based on 100 parts by weight of the second radical monomer, and a weight ratio for mixing the first part and the second part is from 1:10 to 5:1.

3. The divided redox-curing type composition according to claim 1,
   wherein the radical monomer (a) having an acidic group and/or a hydrophilic group has at least one acidic group selected from the group consisting of a phosphoric group, a pyrophosphoric group, a thiophosphoric group, a phosphonic group, a sulfonic group and a carboxylic group, and/or a hydrophilic group.

4. The divided redox-curing type composition according to claim 1,
   wherein the radical monomer (a) having an acidic group and/or a hydrophilic group is at least one radical monomer selected from the group consisting of 10-(meth)acryloyloxydecyl dihydrogen phosphate, 1,3-di(meth) acryloyloxypropyl dihydrogen phosphate, 2-(meth) acryloyloxyethyl dihydrogen phosphate, 4-(meth) acryloyloxyethyl trimellitate anhydride, 4-(meth) acryloyloxyethyl trimellitate, 2-(meth)acrylamide-2-methylpropane sulfonate, 11-(meth) acryloyloxyundecane-1,1-dicarboxylic acid, bisphenol A diglycidyl(meth)acrylate, 2-hydroxyethyl(meth) acrylate, glycerol di(meth)acrylate and 1,2-bis[3-(meth) acryloyloxy-2-hydroxypropyloxy]ethane.

5. A dental adhesive comprising the divided redox-curing type composition of claim 1.

6. The divided redox-curing composition according to claim 1, wherein, said radical monomer (a) comprises a phosphoric group and is at least one monomer selected from the group consisting of 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth) acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate and bis[2-(meth)acryloyloxy-(1-hydroxymethyl)ethyl]hydrogen phosphate, and an acid chloride, an alkali metal salt and an ammonium salt thereof.

7. The divided redox-curing composition according to claim 1, wherein, said radical monomer (a) comprises a pyrophosphoric group and is at least one monomer selected from the group consisting of bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth) acryloyloxyoctyl]pyrophosphate and bis[10-(meth)acryloyloxydecyl]pyrophosphate, an acid chloride, an alkali metal salt and an ammonium salt thereof.

8. The divided redox-curing composition according to claim 1, wherein, said radical monomer (a) comprises a thiophosphoric group and is at least one monomer selected from the group consisting of 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate and 20-(meth)acryloyloxyicosyl dihydrogen thiophosphate, an acid chloride, an alkali metal salt and an ammonium salt thereof.

9. The divided redox-curing composition according to claim 1, wherein, said radical monomer (a) comprises a phosphonic group and is at least one monomer selected from the group consisting of 2-(meth)acryloyloxyethylphenyl phosphonate, 5-(meth)acryloyloxypentyl-3-phosphonopropyonate, 6-(meth)acryloyloxyhexyl-3-phosphonopropyonate, 10-(meth)acryloyloxydecyl-3-phosphonopropyonate, 6-(meth)acryloyloxyhexyl-3-phosphonoacetate and 10-(meth)acryloyloxydecyl-3-phosphonoacetate, an acid chloride, an alkali metal salt and an ammonium salt.

10. The divided redox-curing composition according to claim 1, wherein, said radical monomer (a) comprises a sulfonic group and is at least one monomer selected from the group consisting of 2-(meth)acrylamide-2-methylpropane sulfonate, styrene sulfonic acid and 2-sulfoethyl(meth)acrylate.

11. The divided redox-curing composition according to claim 1, wherein, said radical monomer (a) comprises a carboxyl group and is at least one monomer selected from the group consisting of (meth)acrylic acid, N-(meth)acryloyl glycine, N-(meth)acryloyl aspartate, N-(meth)acryloyl-5- amino-salicylic acid, O-(meth)acryloyl tyrosine, N-(meth)acryloyl tyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid and N-(meth)acryloyl-4-aminosalicylic acid and an acid halide thereof.

12. The divided redox-curing composition according to claim 1, wherein, said radical monomer (a) comprises a plurality of carboxyl groups and is at least one monomer selected from the group consisting of 2-(meth)acryloyloxyethyl hydrogen succinate, 2-(meth)acryloyloxyethyl hydrogen phthalate, 2-(meth)acryloyloxyethyl hydrogen malate, 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate and 2-(meth)acryloyloxyethyl-3'-(meth)acryloyloxy-2'-(3,4-dicarboxybenzoyloxy)propyl succinate and an anhydride and acid halide thereof.

13. The divided redox-curing composition according to claim 1, wherein, said radical monomer (a) comprises a hydrophilic group and is at least one monomer selected from the group consisting of 2-hydroxyethyl(meth)acrylate, 2- or 3-hydroxypropyl (meth)acrylate, 4-hydroxybutyl(meth)acrylate, 5-hydroxypentyl(meth)acrylate, 6-hydroxyhexyl(meth)acrylate, 10-hydroxydecyl(meth)acrylate, 1,2- or 1,3- or 2,3-dihyroxypropane (meth)acrylate, glycerol di(meth)acrylate, 1,2-bis[3-(meth)acryloyloxy-2-hydroxypropyloxy]ethane, diethylene glycol mono(meth)acrylate, triethylene glycol mono(meth)acrylate, tetraethylene glycol mono (meth)acrylate, pentaethylene glycol mono(meth)acrylate, polyethylene glycol mono(meth)acrylate, dipropylene glycol mono(meth)acrylate or polypropylene glycol mono(meth)acrylate; N-methylol (meth)acrylamide, N-(2-hydroxyethyl) (meth)acrylamide, N-(3-hydroxypropyl) (meth)acrylamide, N-(4-hydroxybutyl) (meth)acrylamide, N-(5-hydroxypentyl) (meth)acrylamide, N-(6-hydroxyhexyl) (meth)acrylamide, N-(10-hydroxydecyl) (meth)acrylamide, N-(meth)acryloyl-1,2-dihydroxypropylamine, N-(meth)acryloyl-1,3-dihydroxypropylamine or N-(meth)acryloyl-2,3-dihydroxypropylamine; 2-hydroxy-3-phenoxypropyl(meth)acrylate, 2-hydroxy-3-naphthoxypropyl(meth)acrylate and bisphenol A diglycidyl(meth)acrylate.

14. The divided redox-curing composition according to claim 1, wherein a content of radical monomer (a) is from 5 to 70 wt. %.

15. The divided redox-curing composition according to claim 1, wherein a content of oxidizing agent (b) is from 0.01 to 10 pbw based on 100 pbw of said first radical monomer.

16. The divided redox-curing composition according to claim 1, wherein a content of radical monomer (c) is from 60 to 100%.

17. The divided redox-curing composition according to claim 1, wherein said aromatic sulfinate is a salt of at least one of benzenesulfinic acid, p-toluenesulfinic acid, o-toluenesulfinic acid, ethylbenzenesulfinic acid, decylbenzenesulfinic acid, dodecylbenzenesulfinic acid, 2,4,6-trimethylbenzenesulfinic acid, 2,4,6-triisopropylbenzenesulfinic acid, chlorobenzenesulfinic acid and naphthalenesulfinic acid.

* * * * *